United States Patent [19]

Gopinathan et al.

[11] Patent Number: 6,077,977
[45] Date of Patent: Jun. 20, 2000

[54] METHOD FOR PREPARING HYDROPEROXIDES BY OXYGENATION

[75] Inventors: Sarada Gopinathan, Pune, India; John William Fulmer, Mt. Vernon, Ind.; Changaramponnath Gopinathan, Pune, India; John Christopher Schmidhauser, Easton, Pa.

[73] Assignee: General Electric Company, Schenectady, N.Y.

[21] Appl. No.: 09/088,021

[22] Filed: Jun. 1, 1998

[51] Int. Cl.[7] .................................................. C07G 409/02
[52] U.S. Cl. ............................................. 568/571; 368/568
[58] Field of Search ..................... 568/568, 569, 568/571

[56] References Cited

U.S. PATENT DOCUMENTS

| | | |
|---|---|---|
| 2,548,435 | 4/1951 | Lorand . |
| 2,619,510 | 11/1952 | Armstrong . |
| 2,632,772 | 3/1953 | Armstrong . |
| 2,632,773 | 3/1953 | Armstrong . |
| 2,663,740 | 12/1953 | Calhoun . |
| 2,713,599 | 7/1955 | Lorand . |
| 2,790,004 | 4/1957 | Dougherty . |
| 2,827,493 | 3/1958 | Rindtorff . |
| 2,829,173 | 4/1958 | Shiffler . |
| 2,867,666 | 1/1959 | Erickson . |
| 2,897,239 | 7/1959 | Rovelli . |
| 3,141,046 | 7/1964 | Bichet et al. . |
| 3,171,860 | 3/1965 | Codignola . |
| 3,187,055 | 6/1965 | Armstrong et al. . |
| 3,523,977 | 8/1970 | Reni et al. . |
| 3,907,901 | 9/1975 | Feder et al. . |
| 3,933,921 | 1/1976 | Suda . |
| 4,182,909 | 1/1980 | Angstadt et al. . |
| 4,230,894 | 10/1980 | Young . |
| 4,263,448 | 4/1981 | Leacock . |
| 4,299,991 | 11/1981 | Velenyi et al. . |
| 5,120,902 | 6/1992 | Tagamolila et al. . |
| 5,183,945 | 2/1993 | Stibrany et al. . |
| 5,767,322 | 6/1998 | Mikhailovich . |

FOREIGN PATENT DOCUMENTS

| | | |
|---|---|---|
| 0368292 | 8/1989 | European Pat. Off. . |
| 2708603 | 8/1993 | France . |
| 924449 | 3/1955 | Germany . |

OTHER PUBLICATIONS

CA;127:65386 by Hsu "Polymer supperted catalyst for autoxidation of cumene to cumene hydroperoxide", J. Mol. Catal A: Chem 12091–3) pp. 109–116, 1997.

*Primary Examiner*—Gary Geist
*Assistant Examiner*—Jean F Vollano
*Attorney, Agent, or Firm*—Bernadette M. Bennett; Donald S. Ingraham

[57] ABSTRACT

Aryldialkylmethanes such as cumene are converted to the corresponding hydroperoxides by reaction with oxygen in the presence of a promoter which may be an alkali metal borate such as borax, an alkali metal salt of a polymer such as an acrylic polymer, or an alkaline reagent in combination with a specific proportion of added water or water of hydration, also exemplified by borax. High yields of the hydroperoxide are obtained, particularly when the promoter includes water.

13 Claims, No Drawings

METHOD FOR PREPARING HYDROPEROXIDES BY OXYGENATION

BACKGROUND OF THE INVENTION

This invention relates to the preparation of hydroperoxides, and more particularly to their preparation by an improved oxygenation method.

Hydroperoxides of aryldialkylmethanes such as cumene are valuable intermediates for organic chemicals. Cumene hydroperoxide (hereinafter sometimes "CHP"), for example, may be converted by acid treatment to phenol and acetone, both of which have numerous utilities in the chemical industry. For example, these two compounds can undergo interreaction to form 2,2-bis(4-hydroxyphenyl)propane (bisphenol A), a monomeric precursor of polycarbonates and other polymers.

It has long been known that hydroperoxides of aryldialkylmethanes can be prepared by treatment of the precursor compound with oxygen. The oxygenation reaction typically occurs in the presence of a promoter, most often an aqueous alkaline compound such as sodium hydroxide, sodium carbonate or an alkali metal salt of a carboxylic acid or of cumene hydroperoxide.

Many of the known methods for oxygenation of aryldialkylmethanes are deficient in such respects as yield, reaction rate and tendency to form by-products. It is of interest, therefore, to develop new promoters and methods for treating previously employed promoters so as to improve their behavior and efficiency.

SUMMARY OF THE INVENTION

The present invention is based on a number of discoveries, including the discovery of new promoting materials for the oxygenation reaction and the discovery of a level of water content in the promoting materials which substantially improve yields.

The invention, therefore, is a method for oxidizing an aryldialkylmethane to a hydroperoxide which comprises contacting said aryldialkylmethane with oxygen at a temperature in the range of about 70–125° C. in the presence of an oxidation promoting amount of one of the following:

(I) at least one promoter selected from the group consisting of (A) hydrates of alkali metal borates and (B) alkali metal salts of carboxylic acid-substituted polymers; and (II) an alkaline reagent as promoter in combination with added water or water of hydration, the proportion of said water being about 80–120% by weight based on said alkaline reagent.

DETAILED DESCRIPTION; PREFERRED EMBODIMENTS

The aryldialkylmethanes employed as reactants according to the present invention include those having the formula

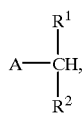

wherein A is an aromatic radical and each of $R^1$ and $R^2$ is an alkyl radical. Suitable aromatic radicals include mononuclear and polynuclear radicals. They may be hydrocarbon or substituted hydrocarbon radicals, including those in which the aromatic ring contains alkyl substituents. The phenyl radical is preferred.

The $R^1$ and $R^2$ radicals are alkyl radicals, most often $C_{1-4}$ primary alkyl radicals. Methyl radicals are preferred. Thus, the especially preferred aryldialkylmethane is cumene (isopropylbenzene). Frequent reference to cumene will be made hereinafter, but it should be understood that other compounds with the above formula may be substituted for cumene when appropriate.

Substantially pure or industrial grade cumene may be employed. It is also possible to employ a cumene stream containing recycled material from previous oxygenation runs. In general, reactant streams containing at least about 90% and preferably at least about 95% cumene by weight are advantageously employed.

Oxygen is another essential reactant in the method of the invention. It may be employed in the form of pure oxygen but more often is present as one constituent of a gaseous mixture such as air.

According to embodiment I of the invention, two classes of materials may be used as promoters. For either class, it is often preferred if not inherent that the promoter be heterogeneous; that is, that it be solid in an otherwise liquid-gaseous reaction mixture.

Class A consists of the hydrates of alkali metal borates. An exemplary and preferred compound is borax; i.e., sodium tetraborate decahydrate, $Na_2B_4O_7 \cdot 10H_2O$.

Class B consists of alkali metal salts, particularly sodium and potassium and preferably sodium salts, of carboxylic acid-substituted polymers. These may be, for example, acrylic polymers; i.e., acrylic acid homopolymers and copolymers. They may also be, for example, polymers of carboxylated styrenes. Copolymers of acrylic acid and acrylamide are especially preferred.

In embodiment II, any alkaline reagent known, either according to the present invention or in the prior art, to be effective as a promoter in the oxygenation reaction is employed in combination with a prescribed amount of water. Alkaline reagents useful as promoters in this embodiment include alkali metal hydroxides such as sodium hydroxide, alkali metal carbonates such as sodium carbonate and alkali metal borates of the type described hereinabove, such as borax.

The amount of promoter employed in the method of the invention is typically in the range of about 1–10% by weight, based on cumene. The amount of water employed in embodiment II, which is critical in this embodiment, is about 80–120% by weight based on alkaline reagent in anhydrous form. This amount may be present as added water, combined with anhydrous alkaline reagent. Alternatively, it may be present as water of hydration, as in borax which contains ten molecules of water of hydration per molecule for a total water content of 90% based on sodium tetraborate.

This proportion of water, when present, results in substantially higher conversion to CHP than when other amounts of water or no water are present. As used herein, "conversion to CHP" is the weight of cumene hydroperoxide found by analysis (e.g., by titration) to be present in the product divided by the weight of cumene as a reactant, expressed as a percentage.

The reaction mixture preferably also contains a small proportion of cumene hydroperoxide as a copromoter. The amount thereof is typically in the range of about 0.5–10.0% by weight based on cumene. Conversion of cumene to cumene hydroperoxide is calculated excluding the amount of hydroperoxide added as copromoter.

The method of the invention is performed by simply contacting the mixture of cumene, promoter, water (when employed) and optionally cumene hydroperoxide with the oxygen-containing gas at a temperature in the range of about 70–125° C., preferably about 70–110° C., in the presence of the promoting materials. Contact may be achieved by simply bubbling the gas through the liquid mixture. For example, a charging apparatus in which the gas enters the mixture through a glass frit may be employed.

When the reaction has proceeded to the desired degree, the product cumene hydroperoxide may be isolated by known techniques. Alternatively, and often preferably, the organic phase of the reaction mixture may be washed to remove alkaline promoter and other impurities and employed directly for the synthesis of phenol and acetone.

The invention is illustrated by the following examples. All parts and percentages are by weight.

EXAMPLES 1–2

A vertical tube reactor containing a fritted glass disk near the bottom and fitted with an air feed tube below the disk and a reflux condenser connected to an ice trap to collect volatile impurities was employed. The reactor was charged with pure (at least 99% by weight) cumene, CHP (82% pure) as copromoter and an aqueous borax solution as promoter. It was heated to 100° C. and air was passed into the mixture at a rate of 67 ml/min for a period of about 6 hours. At the end of that time, the mixture was analyzed for cumene hydroperoxide by titration.

The results are given in Table I, in comparison with a control in which no borax was present. Percentages of borax, CHP and water are based on reactant cumene. "Selectivity" is the proportion of CHP as a percentage of total products formed.

TABLE I

|  | Example | | |
|---|---|---|---|
|  | 1 | 2 | Control |
| Borax, % | 2.5 | 2.5 | — |
| Water, % | 50 | 47.5 | — |
| CHP, % | 4.1 | 10 | 5 |
| Conversion to CHP, % | 6.15 | 6.52 | 3.30 |
| Selectivity, % | 92.47 | 86.30 | 84.64 |

It is apparent that the aqueous borax solutions employed are effective catalysts, affording cumene hydroperoxide at a conversion at about twice that obtained when no promoter is used and a selectivity comparable to the control.

EXAMPLES 3–4

A 300-ml stainless steel autoclave was charged with 100 g of cumene, 2 g of 82% pure cumene hydroperoxide and 5% by weight of two acrylic polymers:

Example 3—poly(acrylamide-acrylic acid), 40% acid groups, sodium salt;

Example 4—polymer of Example 3 combined with 0.5% water.

The mixture was heated to 115° C. and air was passed in at a pressure of 482.7 KPa. After three hours, analysis of the mixture showed a 22.3% conversion to CHP in Example 3, and 28.2% in Example 4. A control employing no acrylic polymer afforded a conversion to CHP of 16.1%.

EXAMPLE 5

The procedure of Examples 1–2 was repeated, employing CHP in the amount of 2% and a promoter comprising 1.25% solid sodium carbonate and 1.25% water. The air flow rate was 64 ml/min and the temperature was 100° C. After 16 hours, the conversion to CHP was 43.34% and the selectivity was 91.04%.

A control in which 2.5% sodium carbonate and 47.5% water was employed as a promoter mixture and 4.1% CHP afforded a conversion to CHP of only 15.52% and a selectivity of 92.62%. Thus, the advantage of employing water in the prescribed amounts for embodiment II is apparent.

EXAMPLES 6–9

The procedure of Examples 1–2 was repeated, employing solid borax (i.e., sodium tetraborate decahydrate) as the catalyst with both pure and recycled (about 98% pure) cumene. Cumene hydroperoxide as a copromoter was introduced at 2%. The results are given in Table II.

TABLE II

|  | Example | | | |
|---|---|---|---|---|
|  | 6 | 7 | 8 | 9 |
| Cumene employed | Pure | Recycled | Recycled | Pure |
| Borax, % | 2.5 | 5.0 | 2.5 | 2.5 |
| Air flow rate, ml/min | 65 | 65 | 65 | 70 |
| Conversion to CHP, % | 43.09 | 57.82 | 33.46 | 49.79 |
| Selectivity, % | 91.27 | 87.88 | 92.15 | 91.80 |

It will be seen that the conversions to CHP were much higher in Examples 6–9, employing water in the proportions defined according to embodiment II, than in Examples 1–2 where water was employed in higher proportions. Selectivities were comparable.

What is claimed is:

1. A method for oxidizing an aryldialkylmethane to a hydroperoxide which comprises contacting said aryldialkylmethane with oxygen at a temperature in the range of about 70–125° C. in the presence of an oxidation promoting amount of at least one promoter selected from the group consisting of (A) hydrates of alkali metal borates and (B) alkali metal salts of carboxylic acid-substituted polymers.

2. A method according to claim 1 wherein the aryldialkylmethane is cumene.

3. A method according to claim 2 wherein the promoter is a hydrate of an alkali metal borate.

4. A method according to claim 3 wherein the promoter is borax.

5. A method according to claim 2 wherein the promoter is an alkali metal salt of an acrylic polymer.

6. A method according to claim 5 wherein the acrylic polymer is an acrylic acid-acrylamide copolymer.

7. A method according to claim 2, wherein cumene hydroperoxide is present as a copromoter.

8. A method according to claim 7 wherein the proportion of cumene hydroperoxide is in the range of about 0.5–10.0% by weight based on cumene.

9. A method according to claim 2, wherein the amount of promoter is about 1–10% by weight based on arydialkylmethane.

10. A method according to claim 2, wherein the oxygen is provided as air.

11. A method according to claim 2, wherein the reaction temperature is in the range of about 70–110° C.

12. A method for oxidizing an aryldialkylmethane to a hydroperoxide which comprises contacting said aryldialkymethane with oxygen at a temperature in a range of about 70–125° C. in the presence of an oxidation promoting amount of borax.

13. A method according to claim 12 wherein the aryldialkylmethane is cumene.

* * * * *